US00PP30668P3

(12) United States Plant Patent
Holmes

(10) Patent No.: US PP30,668 P3
(45) Date of Patent: Jul. 9, 2019

(54) ***CANNABIS* PLANT NAMED 'DD-CT-BR5'**

(50) Latin Name: *Cannabis sativa L.*
Varietal Denomination: DD-CT-BR5

(71) Applicant: Cannagen, LLC, San Gabriel, CA (US)

(72) Inventor: David Holmes, San Gabriel, CA (US)

(73) Assignee: Cannagen, LLC, San Gabriel, CA (US)

( * ) Notice: Subject to any disclaimer, the term of this patent is extended or adjusted under 35 U.S.C. 154(b) by 0 days.

(21) Appl. No.: 15/732,092

(22) Filed: Sep. 15, 2017

(65) Prior Publication Data

US 2019/0090402 P1 Mar. 21, 2019

(51) Int. Cl.

| | |
|---|---|
| ***A01H 5/00*** | (2018.01) |
| ***A01H 6/28*** | (2018.01) |
| ***A61K 36/185*** | (2006.01) |

(52) U.S. Cl.
USPC ..... Plt./263.1
CPC ..... *A01H 6/28* (2018.05); *A61K 36/185* (2013.01)

(58) Field of Classification Search
USPC ..... Plt./263.1
CPC ..... A61K 36/185
See application file for complete search history.

(56) References Cited

PUBLICATIONS https://www.seedsman.com/en/diamonds-dust-regular-seeds Sep. 6, 2016.*
California Cannetics Grow Journal Sonoma Black Dawg. THC Farmer May 22, 2011. pp. 1-53.*
https://www.hytiva.com/strains/sour-bubble Dec. 6, 2018.*
https://www.wikileaf.com/strain/sour-bubble Dec. 6, 2018.*

* cited by examiner

*Primary Examiner* — Annette H Para
(74) *Attorney, Agent, or Firm* — Dickinson Wright PLLC; Kristopher Lance Anderson

(57) ABSTRACT

A new and distinct *Cannabis* plant named 'DD-CT-BR5', comprising numerous racemic inflorescence, particularly distinguished by its trichome density, dried flower yield and max THC content.

4 Drawing Sheets

Genus and species: *Cannabis sativa* L.
Variety denomination: 'DD-CT-BR5'.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

BACKGROUND OF THE NEW PLANT

The present invention relates to a new and distinct cultivar of the *Cannabis* plant, botanically known as *Cannabis sativa* of the Cannabaceae family, and hereinafter referred to by the cultivar name 'DD-CT-BR5'.

Cannabaceae comprises a genus of 9 species including Hops (Humulus). Members of this family can be trees, erect herbs or twining trees (Stevens P. F. 2001). Leaves are often more or less palmately lobed or palmately compound and always bear stipules. Cystoliths are always present and some members of this family possess laticifers.

Cannabaceae are often dioecious (distinct male and female plants). The flowers are actinomorphic (radially symmetrical) and not showy, as these plants are pollinated by the wind. As an adaptation to this kind of pollination, the calyx is short and there is no corolla. Flowers are grouped to form cymes. In the dioecious plants the masculine inflorescences are long and look like panicles, while the feminine are shorter and bear-less flowers. The pistil is made of two connate carpels, the usually superior ovary is unilocular;

there is no fixed number of stamens. There are no petals or sepals on *Cannabis* spp. plants, male or female.

The fruit can be an achene or a drupe.

Asexual propagation of *Cannabis sativa* is often done from off-shoots of a mother plant in the vegetative state. The cloned shoots are then isolated in a humidity dome until roots form and the clone is then transferred to a suitable substrate.

The new *Cannabis sativa* cultivar 'DD-CT-BR5' is a product of a controlled breeding program conducted by the Inventor in Los Angeles Calif., USA. The objective of the program was to develop a new *Cannabis sativa* cultivar that has a trichome density similar to the Sour Bubble parent and preserves the dominant terpenes Limonene and b-Caryophyllene but has a higher yield, increased vigor and a higher total max Tetrahydrocannabinol (THC). The new plant, 'DD-CT-BR5' originated from a cross made in 2015 in East Los Angeles Calif. The female or seed parent is the *Cannabis sativa* cultivar, ssp. *indica*, designated "Sour Bubble", unpatented. The male or pollen parent is *Cannabis sativa* cultivar designated, "DDL19(2)", unpatented. The new *Cannabis sativa*, 'DD-CT-BR5' was discovered and selected by the inventor as a single flowering plant within the progeny of the stated cross in a controlled environment in 2015 in East Los Angeles Calif.

Asexual reproduction of the new *Cannabis sativa* cultivar by cloning of the terminal or axillary bud, was first performed in November, 2015 in East Los Angeles Calif., and has demonstrated that the combination of characteristics as herein disclosed for the new cultivar are firmly fixed and retained through successive generations of asexual reproduction. The new cultivar asexually reproduces true-to-type.

SUMMARY OF THE INVENTION

The following traits have been repeatedly observed and are determined to be unique characteristics of 'DD-CT-BR5' which in combination distinguish this *Cannabis sativa* as a new and distinct plant.

1) Flowers which have green to light green bracts with purplish hues and dark green leaflets. The stigmas protruding from the bracts are a reddish orange color.
2) The plant produces more than one inflorescence
3) The plants can be propagated economically and uniformly using asexual means such as cloning or tissue culture.
4) The plant has a high flower yield per square foot of canopy.

In comparison with the parental cultivars of 'DD-CT-BR5', the female parent "Sour Bubble" only yields 21.7 grams per square feet of canopy while 'DD-CT-BR5' yields 71.3 grams per square feet of canopy. The male parent possesses a maximum THC content of 1.27%, while 'DD-CT-BR5' contains 22.29% THC.

Presently, the most commercially similar cultivars to 'DD-CT-BR5' is the female parent cultivar "Sour Bubble", to which a comparison has already been provided.

BRIEF DESCRIPTION OF THE PHOTOGRAPHS

The accompanying pictures illustrate the overall appearance of the new *Cannabis sativa* 'DD-CT-BR5' showing the colors as reasonably possible with colored reproductions of this type. Colors in the photographs may differ slightly from the color values cited in the detailed botanical description, which accurately described the colors of 'DD-CT-BR5'.

Figure 1:
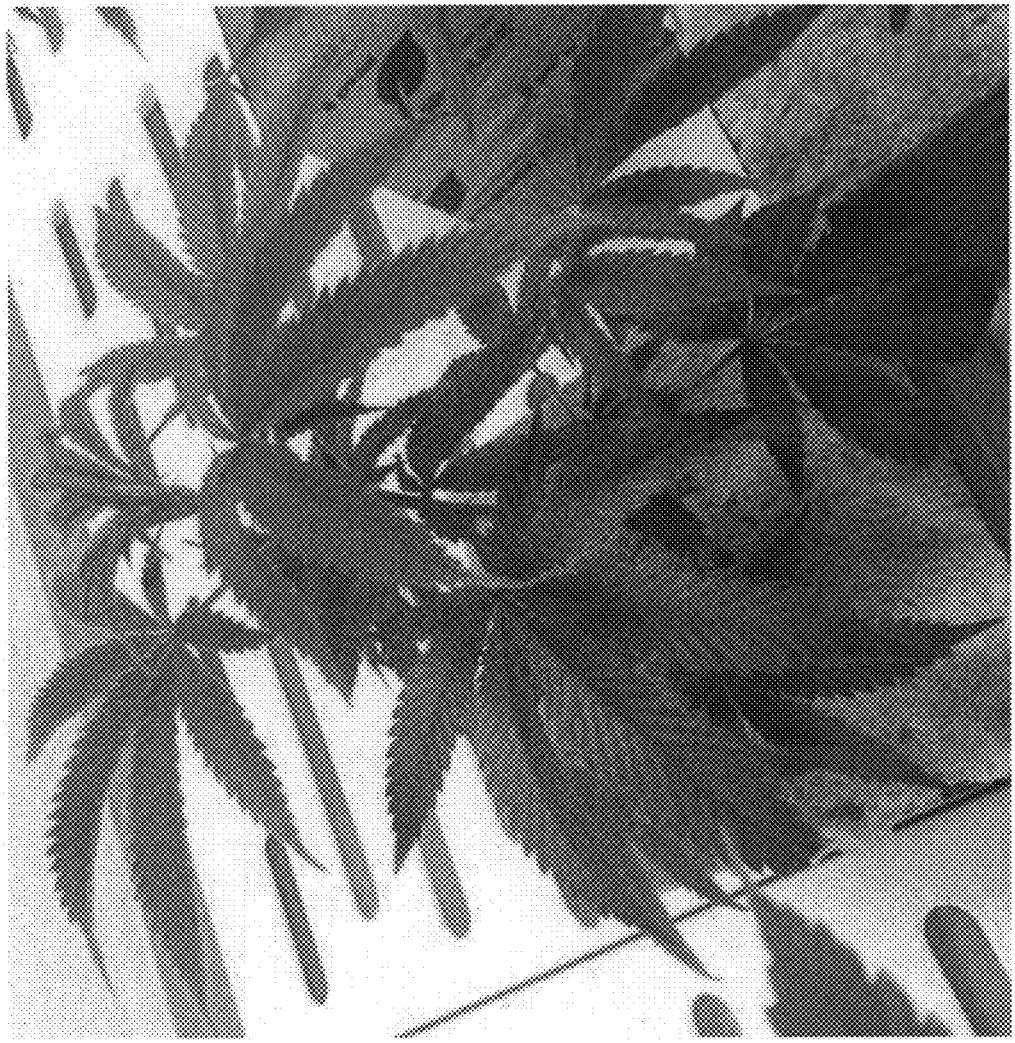
FIG. 1 shows a whole plant view of 'DD-CT-BR5' in vegetative stage.
Figure 2:
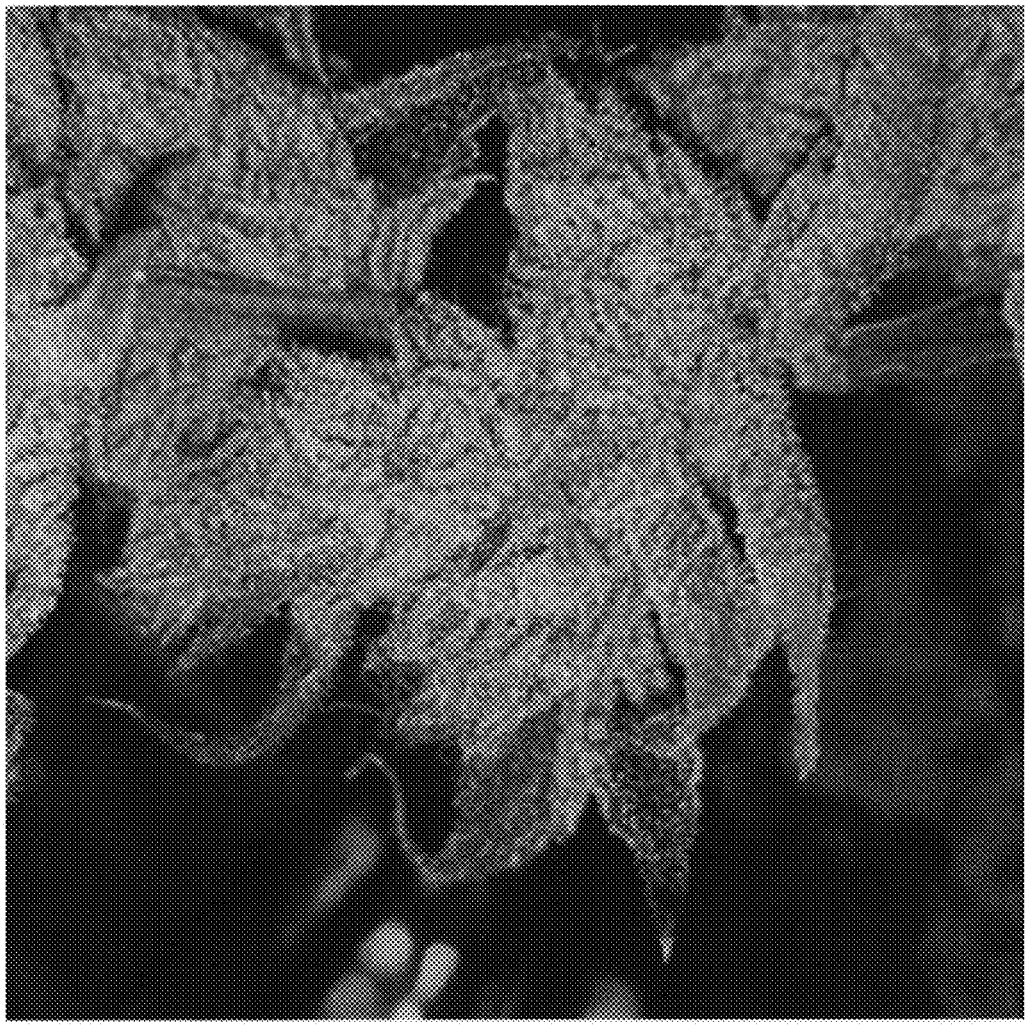
FIG. 2 shows a close up view of the typical inflorescence of 'DD-CT-BR5'.

The foregoing and other features and advantages of the plant will be apparent from the following detailed botanical description, as illustrated in the accompanying photographs.

DETAILED BOTANICAL DESCRIPTION

The new *Cannabis sativa* cultivar 'DD-CT-BR5' has not been observed under all possible environmental conditions. However, the plants were grown under environmental conditions and cultural practices which approximate those generally used in commercial *Cannabis* grow operations. The phenotype of the new cultivar may vary depending on the environmental conditions such as temperature, humidity, light intensity and photoperiod without any change made to the genotype of the plant.

The aforementioned photographs, together with the following observations, measurements and values describe plants of 'DD-CT-BR5' as grown under artificial lighting with a DLI of approximately 25 mols, temperatures between 70° F. and 80° F., VPD of 8 KPA and a balanced fertilizer with 150 ppm N, 40 ppm P, 200 ppm K, 150 ppm Ca, 50 ppm S. Duration of growth of 'DD-CT-BR5' from potting size is between 11 and 13 weeks.

Color references are made to The Royal Horticultural Society Colour Chart (R.H.S.), $6^{th}$ edition, except where general colors of ordinary significance are used. Color values were taken under daylight conditions at approximately noon in Los Angeles, Calif. The age of the plants described is 12 weeks after potting.

Classification:

*Family*.—Cannabaceae.

*Botanical*.—*Cannabis sativa*.

Parentage: Female Parent, *Cannabis sativa* cultivar, spp. *indica* designated "Sour Bubble", unpatented. Male Parent, *Cannabis sativa* cultivar designated "DDL19(2)" aka "Double Dream x Lemon Haze x Bubblegum", unpatented.

Propagation:

*Type*.—Asexual (Vegetative Cuttings; Cloning).

*Rooting habit and description*.—freely branching and fibrous. It takes approximately 14 to 21 days after cloning to initiate roots.

Plant:

a) *Size and maturity*.—i) Height — 1371.6 mm ii) Width (Spread) — 609.5 mm iii) Stem Width and Color — Width=27.29 mm and color is RHS NN137D with venation color RHS N79A.

b) *Growth habit*.—Upright plant. Intermediate to tall plant size. Green leaves (RHS NN137A and RHS 139A). Larger than average Racemes.

c) *Crop time*.—Following asexual reproduction it takes approximately 3 weeks for the development of the first new leaf set. It takes about 18 days at 78° F. temperature during the 12 hour photoperiod for the first set of racemes to appear.

Figure 3:
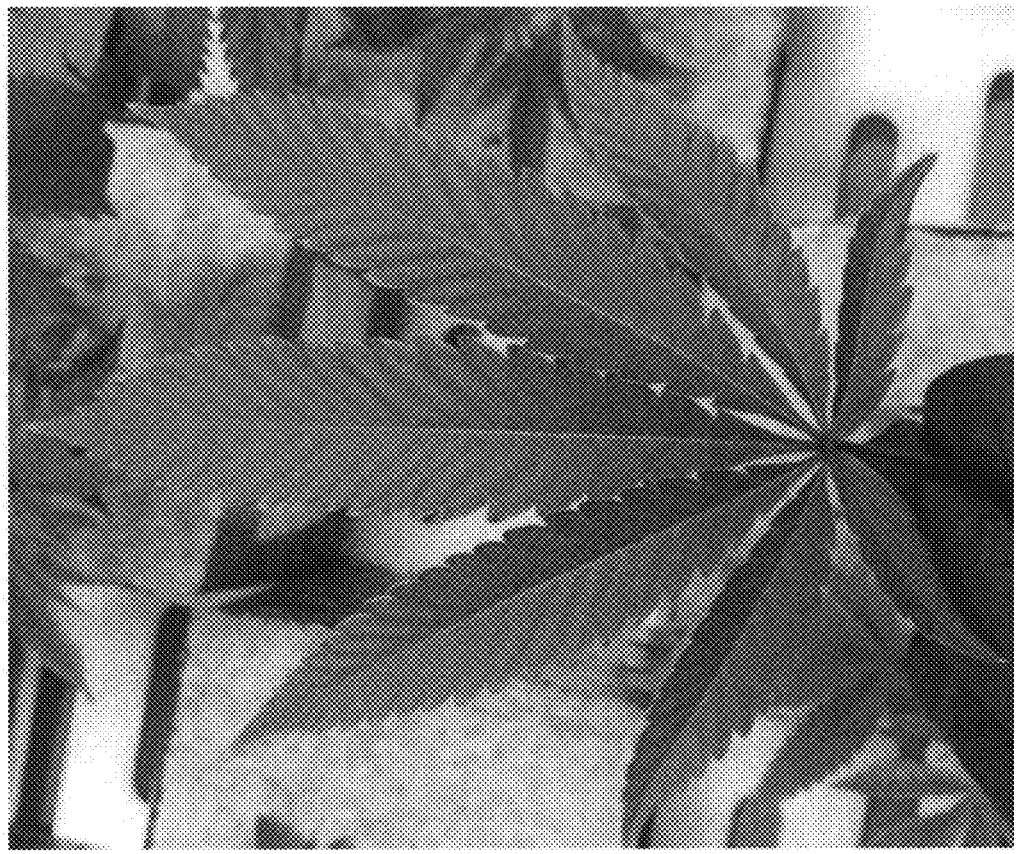
FIG. 3 shows a close up of the typical leaves of 'DD-CT-BR5'.
Figure 4:
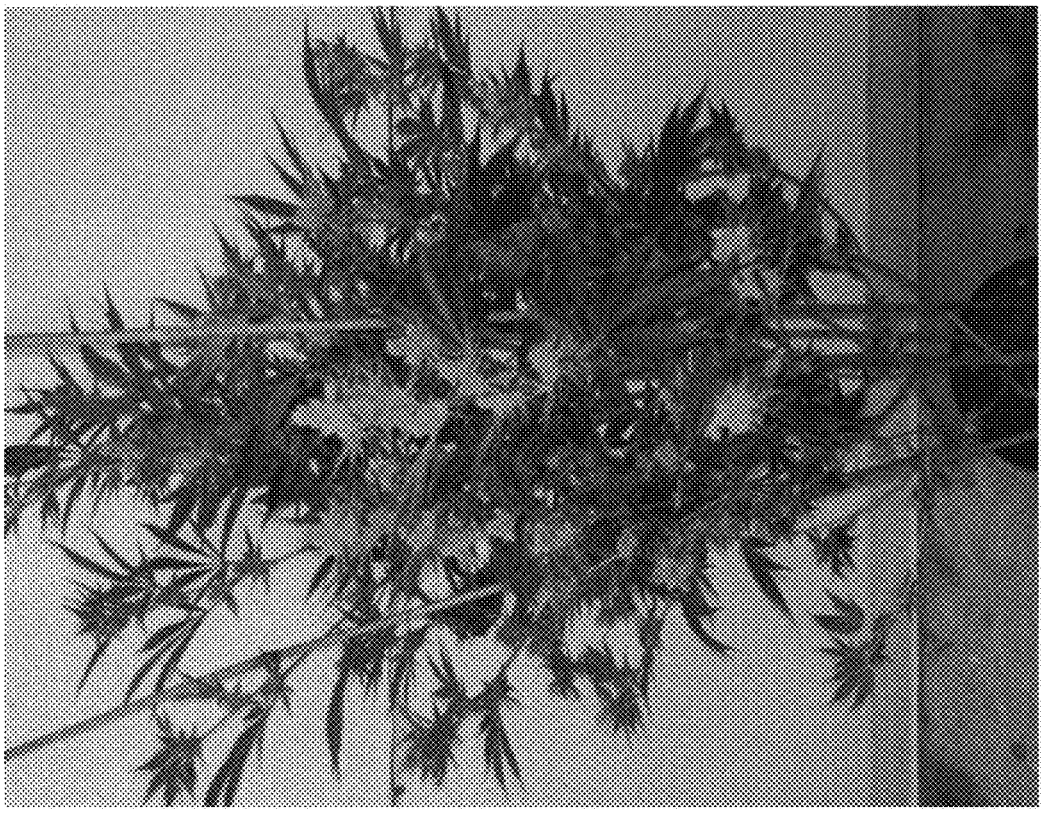
FIG. 4 shows a whole plant view of a female plant of 'DD-CT-BR5' in inflorescence stage.

Foliage:

a) *Quantity per plant*.—Each compound leaf has 5 to 7 leaflets.

b) *Arrangements and attachment*.—The branches alternate along the main stem and there is no even symmetry in plants that have been reproduced by cloning. The original plant from seed had even symmetry in the vegetative state but then changed to an alternating style.

c) *Overall shape of leaf*.—The leaves have even symmetry and serrated leaf margins (see FIG. 3).

d) *Texture* (*both surfaces*).—The leaves have a rough surface and are covered in bulbous glandular trichomes which give the leaf a sticky sensation.

e) *Mature leaf length*.—164.2 mm.

f) *Mature leaf/leaflet width*.—197.42 mm.

g) *Mature leaf thickness*.—0.42 mm (Small leaf average). 0.67 mm (Midsize Leaf Average). 1.11 mm (Large Leaf average).

h) *Mature leaf color*.—RHS NN137A and 139A, Underside of the leaf has color RHS NN137D.

i) *Venation*.—Pattern: Parallel with even symmetry along main vein. Color of midvein: Upper Side: (RHS NN137D). Underside: (RHS NN137D).

Raceme:

a) *Quantity per plant*.—Average is 90 per plant.

b) *Number of flowers per raceme*.—Average of 2.5.

c) *Length*.—55.69 mm to 93.89 mm dependent on location.

d) *Diameter*.—At or near 33.5 mm.

e) *Aspect*.—Primarily vertical; secondarily acutely angular (<90° from vertical).

f) *Color*.—RHS 137D with hues of RHS N79A.

g) *Internode*.—Length: Various internode lengths. On the main stem, the internode spacing ranges from 56.04 mm to 147.89 mm. For branches the internode spacing is at or near 55 mm.

h) *Flowers per plant*.—Average is 225 per plant.

Inflorescence description:

a) *Appearance*.—Stacking, racemose inflorescence with cylindrical cone shaped structure that open in succession beginning with the lowermost flower.

b) *Florescence*.—There are no petals or sepals on *Cannabis*, spp. plants, male or female. i) Height (From base to tip) — 73.28 mm. ii) Diameter (at midpoint). — 38.5 mm. iii) Shape — Ovate. iv) Color — RHS 137D with hues of RHS N79A. v) Orientation — The plant grows upright/vertical with axillary shoots growing at a 45 degree angel from the meristem.

c) *Flowering times*.—For a plant flowering at temperatures around 80° F. for 4 weeks and 70° F. for 4 to 6 weeks, racemes appear at around day 18 of the flowering period. Flowers stigmas are close to 100% shriveled by week 9 of the flowering period. Peak cannabinoid output occurs between weeks 9 and 10 of the flowering period.

d) *Flower longevity*.—Flowers remain open for around 50 to 60 days before they start to wither.

e) *Fragrance*.—The aroma emitted from the flowers smells similar to lemon citrus with hints of gasoline.

f) *Flower rate of opening*.—Flowers usually open about 16 to 18 days after bract separation.

TABLE 1

Cannabinoid levels of Parents and Claimed Plant - 'DD-CT-BR5'.

| Strain | Sex | Max THC % | [Max CBD%] | [Max CBG%] | [Sum Terpenes mg/g] |
|---|---|---|---|---|---|
| Sour Bubble (SB7) | F - Parent (P1) | 14.41 | [0.25] | [0.40] | [37.41] |
| DDL19(2) | M - Parent (P1) | 1.27 | [0.01] | [0.42] | [2.93] |
| DD-CT-BR5 | F - Offspring (F1) | 22.29 | [0.49] | [1.55] | [19.44] |

Cannabinoid and terpene levels provided in Table 1 above were obtained via analysis of dried flower material, utilizing high performance liquid chromatography (HPLC) and gas chromatography mass spectrometry (GC-MS).

TABLE 2

Terpenes/Terpenoids of Claimed Plant - 'DD-CT-BR5'

| Terpenes | mg/g |
|---|---|
| α-Bisabolol | 0.19 |
| Camphene | 0.18 |
| Campher | 0.02 |
| β-Caryophyllene | 2.09 |
| Caryophyllene oxide | 0.53 |
| α-Cedrene | 0.01 |
| β-Eudesmol | 0.76 |
| β-Fenchol | 0.49 |
| Guaiol | 0.13 |
| α-Humulene | 0.12 |
| Isoborneol | 0.11 |
| Limonene | 5.13 |
| Linalool | 2.13 |
| Menthol | 0.02 |
| Myrcene | 1.84 |
| Nerol | 0.01 |
| α-Pinene | 0.57 |
| β-Pinene | 1.14 |
| Sabinene Hydrate | 0.02 |
| α-terpineol | 0.57 |
| Terpinolene | 0.05 |
| α-Guaiene (t) | 0.12 |
| Elemene (t) | 0.43 |
| Farnesene (t) | 0.75 |
| Guaia-1(10), 11-diene (t) | 0.07 |
| Selina-3, 7(11)-diene (t) | 0.86 |
| Valencene (t) | 1.08 |
| Sum of Terpenes | 19.44 |

Terpene/Terpenoid amounts provided in Table 2 above were obtained via analysis of dried flower material, utilizing high performance liquid chromatography (HPLC) and gas chromatography mass spectrometry (GC-MS).

Reproductive organs:

a) *Arrangement*.—The flowers are dense collections of bracts with protruding stigmas. Within each bract is an ovule attached to two stigmas. Bracts are densely covered with capitate stalked, capitate sessile and bulbous trichomes.

Temperature tolerance:

a) *High temperatures*.—This variety can continue to grow in temperatures as high as 95 F but even limited exposure to temperatures in this range will show reduced growth rates.

b) *Low temperatures*.—This variety will continue to grow in temperatures as low as 62 F but below this temperature the growth rate will decrease dramatically.

What is claimed is:

1. A new and distinct *Cannabis sativa* plant named 'DD-CT-BR5', as illustrated and described herein.

* * * * *